(12) United States Patent
Hou et al.

(10) Patent No.: US 8,867,837 B2
(45) Date of Patent: Oct. 21, 2014

(54) DETECTING SEPARATOR LINES IN A WEB PAGE

(75) Inventors: Hui-Man Hou, Beijing (CN); Li-Wei Zheng, Beijing (CN); Jian-Ming Jin, Beijing (CN); Jian Fan, Palo Alto, CA (US); Suk Hwan Lim, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 73 days.

(21) Appl. No.: 13/812,421

(22) PCT Filed: Jul. 30, 2010

(86) PCT No.: PCT/CN2010/001156
§ 371 (c)(1),
(2), (4) Date: Jan. 25, 2013

(87) PCT Pub. No.: WO2012/012915
PCT Pub. Date: Feb. 2, 2012

(65) Prior Publication Data
US 2013/0163873 A1   Jun. 27, 2013

(51) Int. Cl.
*G06K 9/34* (2006.01)
*C07D 309/28* (2006.01)
*G06K 9/00* (2006.01)

(52) U.S. Cl.
CPC .......... *G06K 9/00463* (2013.01); *C07D 309/28* (2013.01)
USPC ............................ 382/173; 382/175; 382/176

(58) Field of Classification Search
None
See application file for complete search history.

(56) References Cited

U.S. PATENT DOCUMENTS

| 6,108,675 | A  | * | 8/2000  | Gregg et al. ................. 715/234 |
| 6,711,292 | B2 |   | 3/2004  | Wang |
| 7,246,306 | B2 |   | 7/2007  | Chen et al. |
| 2002/0159636 | A1 | * | 10/2002 | Lienhart et al. ............... 382/176 |
| 2004/0205608 | A1 |   | 10/2004 | Huang |
| 2005/0028077 | A1 | * | 2/2005  | Wen et al. ................. 715/500.1 |

(Continued)

FOREIGN PATENT DOCUMENTS

| CN | 1577328 A | 2/2005 |
| CN | 1852245 A | 10/2006 |
| CN | 101576933 A | 11/2009 |

OTHER PUBLICATIONS

Pnueli, Ayelet, et al. "Web page layout via visual segmentation." HP Laboratories (2009).*

Liu, Xinyue, Hongfei Lin, and Ye Tian. "Segmenting webpage with Gomory-Hu tree based clustering." Journal of Software 6.12 (2011): 2421-2425.*

(Continued)

*Primary Examiner* — Li Liu

(57) ABSTRACT

A system and method of detecting separator lines in a web page may include determining coordinates of visible web elements on a web page, generating an edge image of the web page based on the coordinates of the web elements, filtering edges belonging to non-separator line elements within the edge image, detecting horizontal lines within the edge image, detecting vertical lines within the edge image, and filtering short lines within the edge image. A system for detecting separator lines in a web page may include a memory device, and a processor communicatively coupled to the memory, in which the processor determines coordinates of visible web elements on a web page, generates an edge image of the web page based on the coordinates of the web elements, filters edges belonging to non-separator line elements within the edge image, detects horizontal lines within the edge image, detects vertical lines within the edge image, and filters short lines within the edge image.

20 Claims, 8 Drawing Sheets

(56) References Cited

U.S. PATENT DOCUMENTS

| | | | |
|---|---|---|---|
| 2008/0270890 A1* | 10/2008 | Stern | 715/239 |
| 2009/0022394 A1 | 1/2009 | Banerjee et al. | |
| 2009/0259926 A1* | 10/2009 | Deliyannis | 715/205 |
| 2010/0080411 A1* | 4/2010 | Deliyannis | 382/100 |
| 2013/0124953 A1* | 5/2013 | Fan et al. | 715/202 |
| 2013/0283148 A1* | 10/2013 | Lim et al. | 715/234 |

OTHER PUBLICATIONS

Deng Cai et al, "VIPS: A Vision-Based Page Segmentation Algorithm", Nov. 1, 2003.

Jiuxin, Cao et al, "A Segmentation Method for Web Page Analysis Using Shrinking and Dividing", Apr. 2010, V.25, 93-104.

Yu Chen et al, "Detecting Web Page Structure for Adaptive viewing on Small Form Factor Devices", May 20, 24, 2003.

* cited by examiner

DETECTING SEPARATOR LINES IN A WEB PAGE

BACKGROUND

Web pages located on the World Wide Web and accessed via the Internet include a variety of content including text, images, and other forms of multimedia. These web pages are often divided into multiple portions or regions by horizontal lines, vertical lines, and frames. These lines are referred to as "separator lines."

When viewed in terms of web page design, content located within the different regions of the web page defined by the separator lines have different semantic meanings (i.e., the relationships of characters or groups of characters to their meanings, independent of the manner of their interpretation and use) or document functions (e.g., a portion of an article or a sidebar). Being able to detect separator lines within the web pages is very useful in subsequent processing of a web page including, for example, web page printing, block level based web page searching, web page segmentation, and many other applications.

BRIEF DESCRIPTION OF THE DRAWINGS

The accompanying drawings illustrate various examples of the principles described herein and are a part of the specification. The illustrated examples are merely examples and do not limit the scope of the claims.

Throughout the drawings, identical reference numbers designate similar, but not necessarily identical, elements.

DETAILED DESCRIPTION

Figure 1:
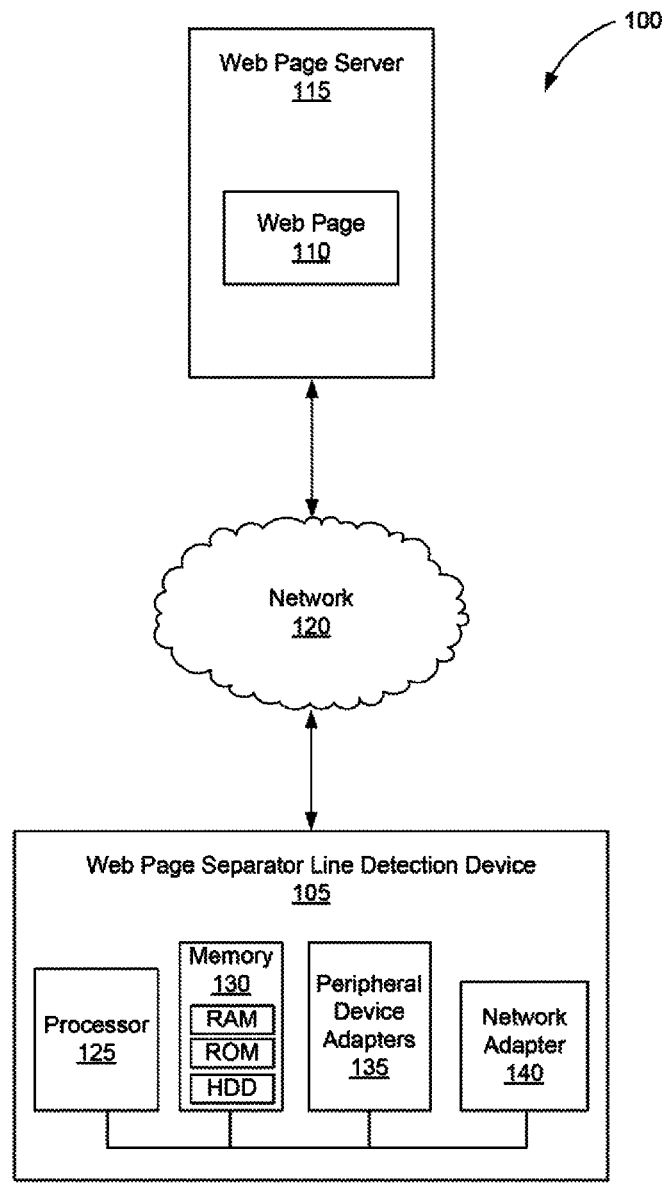
FIG. 1 is a block diagram of an illustrative system for detecting separator lines in a web page, according to one example of principles described herein.

The present specification discloses various methods, systems, and devices for detecting separator lines in a web page. As discussed above, detect separator lines within the web pages is very useful in subsequent processing of a web page including, for example, web page printing, block level based web page searching, web page segmentation, and many other applications.

There are a number of challenges in detecting separator lines in a web page. For example, web pages vary widely by content type. Common types of web pages include: news, shopping, blog, map, and recipe web pages. The web page layouts also vary widely across the different types of web pages. The web pages also included a variety of content, including text, images, video and flash. To effectively detecting separator lines in a web page, no previous solution is disclosed.

Thus, a method of detecting separator lines in a web page, according to the example of principles described herein, may include determining coordinates of visible web elements on a web page, generating an edge image of the web page based on the coordinates of the web elements, filtering edges belonging to non-separator line elements within the edge image, detecting horizontal lines within the edge image, detecting vertical lines within the edge image, and filtering short lines within the edge image. A system for detecting separator lines in a web page may include a memory device, and a processor communicatively coupled to the memory, in which the processor determines coordinates of visible web elements on a web page, generates an edge image of the web page based on the coordinates of the web elements, filters edges belonging to non-separator line elements within the edge image, detects horizontal lines within the edge image, detects vertical lines within the edge image, and filters short lines within the edge image.

As used in the present specification and in the appended claims, the term "web page" refers to a document that can be retrieved from a server over a network connection and viewed in a web browser application. Further, as used in the present specification and in the appended claims, the term "node" refers to one of a plurality of coherent units into which the entire content of a web page has been partitioned.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example," "an example" or similar language means that a particular feature, structure, or characteristic described in connection with the example or example is included in at least that one example, but not necessarily in other examples. The various instances of the phrase "in one example" or similar phrases in various places in the specification re not necessarily all referring to the same example.

According to one example of principles described herein, a computer readable storage medium may be, for example, but not limited to, an electronic, magnetic, optical, electromagnetic, infrared, or semiconductor system, apparatus, or device, or any combination thereof. More specifically, the computer readable storage medium may be an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any combination thereof. In the context of this document, a computer readable storage medium may be any tangible medium that can contain, or store a program for use by or in connection with an instruction execution system, apparatus, or device.

Program code embodied on a computer readable medium may be transmitted using any appropriate medium, including but not limited to wireless, wired, optical fiber cable, RF, etc., or any suitable combination of the foregoing. Computer program code for carrying out operations of the present invention may be written in an object oriented programming language such as Java, Smalltalk, C, C++, among others. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

Computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Referring now to FIG. 1, an illustrative system (100) for detecting separator lines in a web page may include a web page separator line detection device (105) that has access to a web page (110) stored by a web page server (115). In the present example, for the purposes of simplicity in illustration, the web page separator line detection device (105) and the web page server (115) are separate computing devices communicatively coupled to each other through a mutual connection to a network (120). However, the principles set forth in the present specification extend equally to any alternative configuration in which a web page separator line detection device (105) has complete access to a web page (110). As such, alternative examples within the scope of the principles of the present specification include, but are not limited to, examples in which the web page separator line detection device (105) and the web page server (115) are implemented by the same computing device, examples in which the functionality of the web page separator line detection device (105) is implemented by a multiple interconnected computers (e.g., a server in a data center and a user's client machine), examples in which the web page separator line detection device (105) and the web page server (115) communicate directly through a bus without intermediary network devices, and examples in which the web page separator line detection device (105) has a stored local copy of the web page (110) to be analyzed.

In one example utilizing a network (120), the network (120) may be any number of computing devices or elements physically connected for the purpose of exchanging data. The network (120) may include, for example, a local area network (LAN), a wide area network (WAN), a virtual private network (VPN), and the Internet, among others.

The web page separator line detection device (105) of FIG. 1 may be a computing device that retrieves the web page (110) hosted by the web page server (115) and detect separator lines within the web page (110). In the present example, this is accomplished by the web page separator line detection device (105) first requesting the web page (110) from the web page server (115) over the network (120) using the appropriate network protocol (e.g., Internet Protocol ("IP")). Illustrative processes of detecting separation lines will be set forth in more detail below.

To achieve its desired functionality, the web page separator line detection device (105) includes various hardware components. Among these hardware components may be at least one processor (125), at least one memory unit (130), peripheral device adapters (135), and a network adapter (140). These hardware components may be interconnected by one or more busses and/or network connections.

The processor (125) may include the hardware architecture necessary to retrieve executable code from the memory unit (130) and execute the executable code. The executable code may, when executed by the processor (125), causes the processor (125) to implement at least the functionality of retrieving the web page (110) and detecting separation lines within the web page (110) according to the methods of the present specification described below. In the course of executing code, the processor (125) may receive input from and provide output to one or more of the remaining hardware units.

The memory unit (130) may digitally store data consumed and produced by the processor (125). The memory unit (130) may include various types of memory modules, including volatile and nonvolatile memory. For example, the memory unit (130) of the present example includes Random Access Memory (RAM), Read Only Memory (ROM), and Hard Disk Drive (HDD) memory. As discussed above, many other types of memory are available in the art, and the present specification contemplates the use of any type(s) of memory (130) in the memory unit (130) as may suit a particular application of the principles described herein. In certain examples, different types of memory in the memory unit (130) may be used for different data storage needs. For example, in certain examples the processor (125) may boot from ROM, maintain nonvolatile storage in the HDD memory, and execute program code stored in RAM.

The hardware adapters (135, 140) in the web page separator line detection device (105) enable the processor (125) to interface with various other hardware elements, external and internal to the web page separator line detection device (105). For example, peripheral device adapters (135) may provide an interface to input/output devices to create a user interface and/or access external sources of memory storage. Peripheral device adapters (135) may also create an interface between the processor (125) and, for example, a printer, display device, or other peripheral device.

Figure 2:
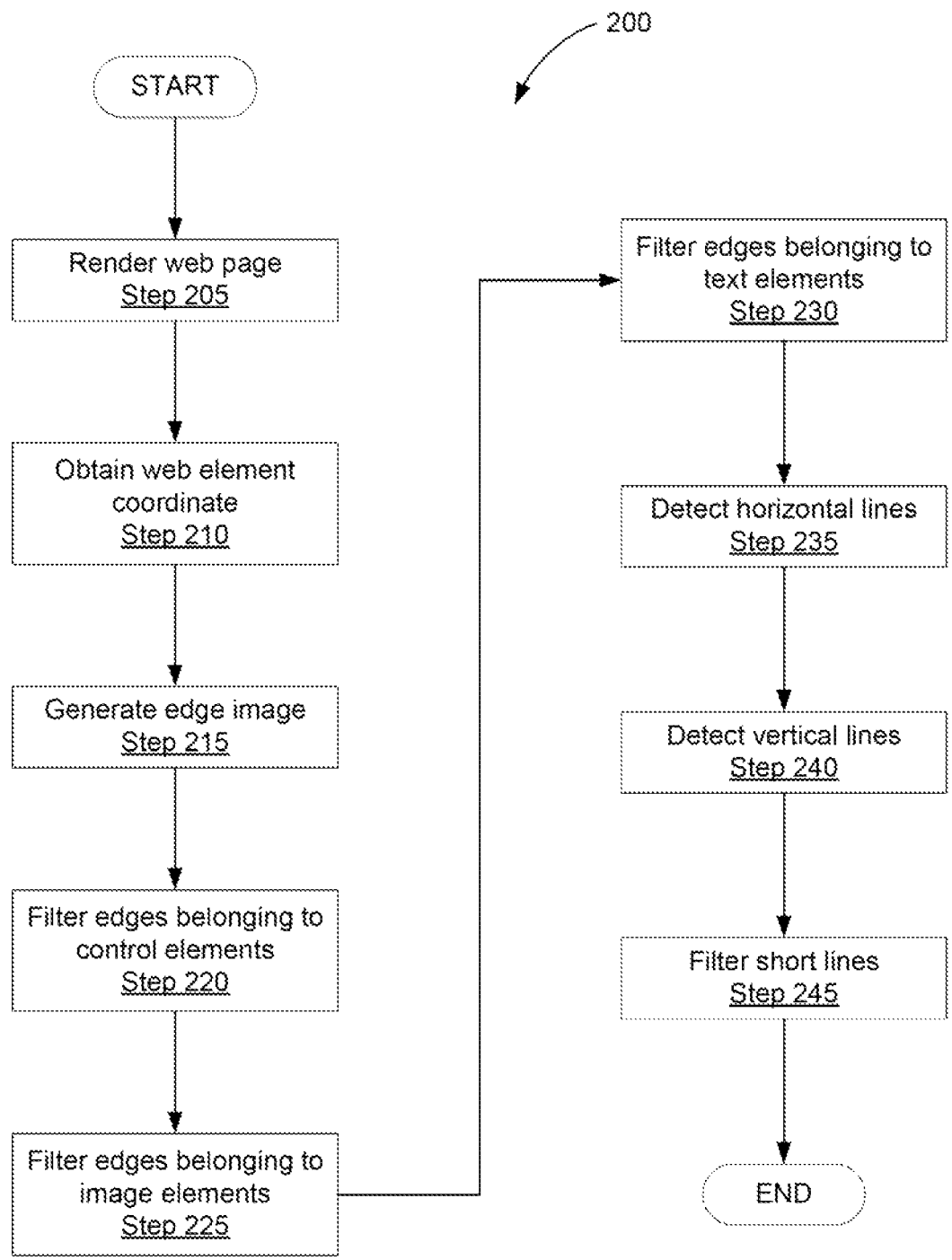
FIG. 2 is a flowchart depicting an illustrative separator line detection method, according to one example of principles described herein.

A network adapter (140) may provide an interface to the network (120), thereby enabling the transmission of data to and receipt of data from other devices on the network (120), including the web page server (115). The web page server may be any combination of hardware and software capable of servicing Hypertext Transfer Protocol (HTTP) requests FIG. 2 is a flowchart depicting an illustrative separator line detection method (200), according to one example of principles described herein. The method may begin by rendering a web page (110) (Step 205). This may be accomplished by, for example, the web page separator line detection device (105) of FIG. 1 in which the web page separator line detection device (105) retrieves the web page (110) hosted by the web page server (115). More specifically, the web page separator line detection device (105) may include a web browser stored in memory (130). The web browser is a client program that initiates requests for a web page (110) to a web page server (115) via the network (120), and renders and displays the web page (110) that the server returns. The web browser may be WINDOWS® INTERNET EXPLORER® (using the TRI- DENT® engine), MOZILLA® FIREFOX® (using the GECKO® engine), or WEBKIT®, for example.

Next, the web page separator line detection device (105) obtains the coordinates of the various web elements within the web page (110) (Step 210). This may be accomplished by, for example, a software product for obtaining the rendering co-ordinates of visible text elements on a web page executed by the processor (125). This software product may comprise three modules: a tag wrapper module, a co-ordinate calculator module, and an invisible text element filter. These modules work together to produce a data structure containing details of the text nodes and their co-ordinates, in which the invisible text nodes are filtered out.

To do this, the tag wrapper module queries each text node of a data structure representing a web page (110) rendered by a browser using the document object module (DOM) application program interface (API). Thus, the tag wrapper module waits until any Cascading Style Sheet (CSS) information has been applied to the HTML and until any scripts (such as JavaScript) have been executed. The tag wrapper module then wraps each text node in a pair of HTML tags. It produces a JavaScript Object Notation (JSON) data structure as output, which comprises all the text nodes wrapped in the HTML tags (along with all the other nodes representing the HTML). Under some circumstances, the web page (110) may be re-rendered to incorporate the wrapped text nodes correctly. If this is done, then the tag wrapper module adds the pairs of HTML tags to the text nodes in the data structure via the DOM API and then instructs the browser to re-render the web page including the additional pairs of HTML tags.

The JSON data is then received by the co-ordinate calculator module. The co-ordinate calculator module then obtains co-ordinates for each text node and attaches them as attributes to the data structure via the DOM API. Lastly, the invisible text element filter determines whether each text node is invisible and if it is, it excludes the text element from an output data structure, which is in the form of a list of visible text nodes to which are attached the co-ordinates calculated by co-ordinate calculator module (along with any other attributes already present from the original data structure). Alternatively, or in addition, the data structure may be modified by deletion of the invisible text nodes.

Figure 3:
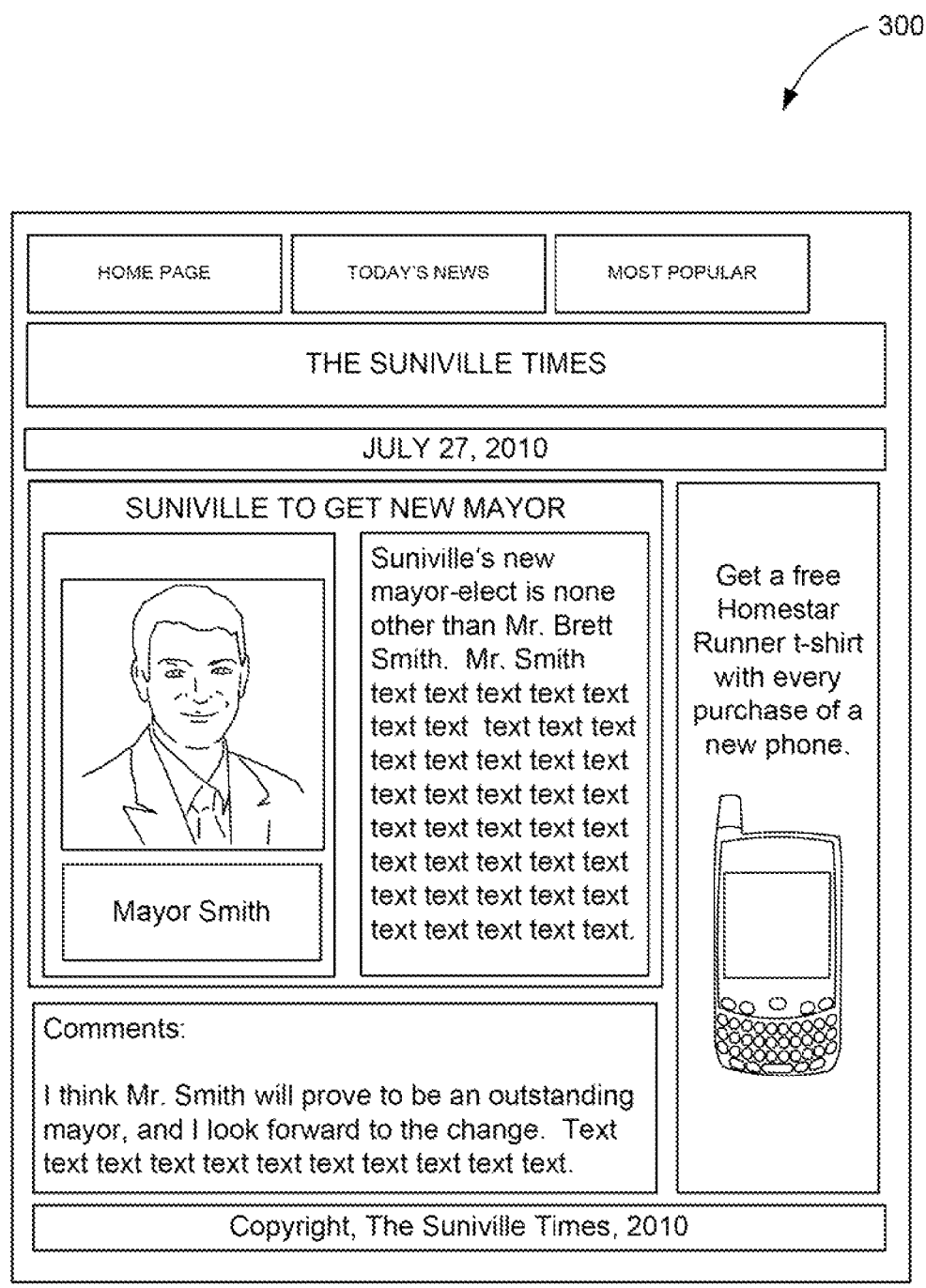
FIG. 3 is a depiction of a grayscale rendered image, according to one example of principles described herein.

After, the coordinates of the various web elements within the web page have been identified and obtained (Step 210), an edge image of the rendered web page may be generated (Step 215). This step may include first converting the rendered web page into an image. The processor (125), or an image processor (not shown) may perform this conversion. The rendered web page may be converted into, for example, a grayscale image (300) as depicted in FIG. 3 by, for example, the processor (125). In other examples, the rendered web page may be converted into any type of image including, for example, color or binary images.

Figure 4:
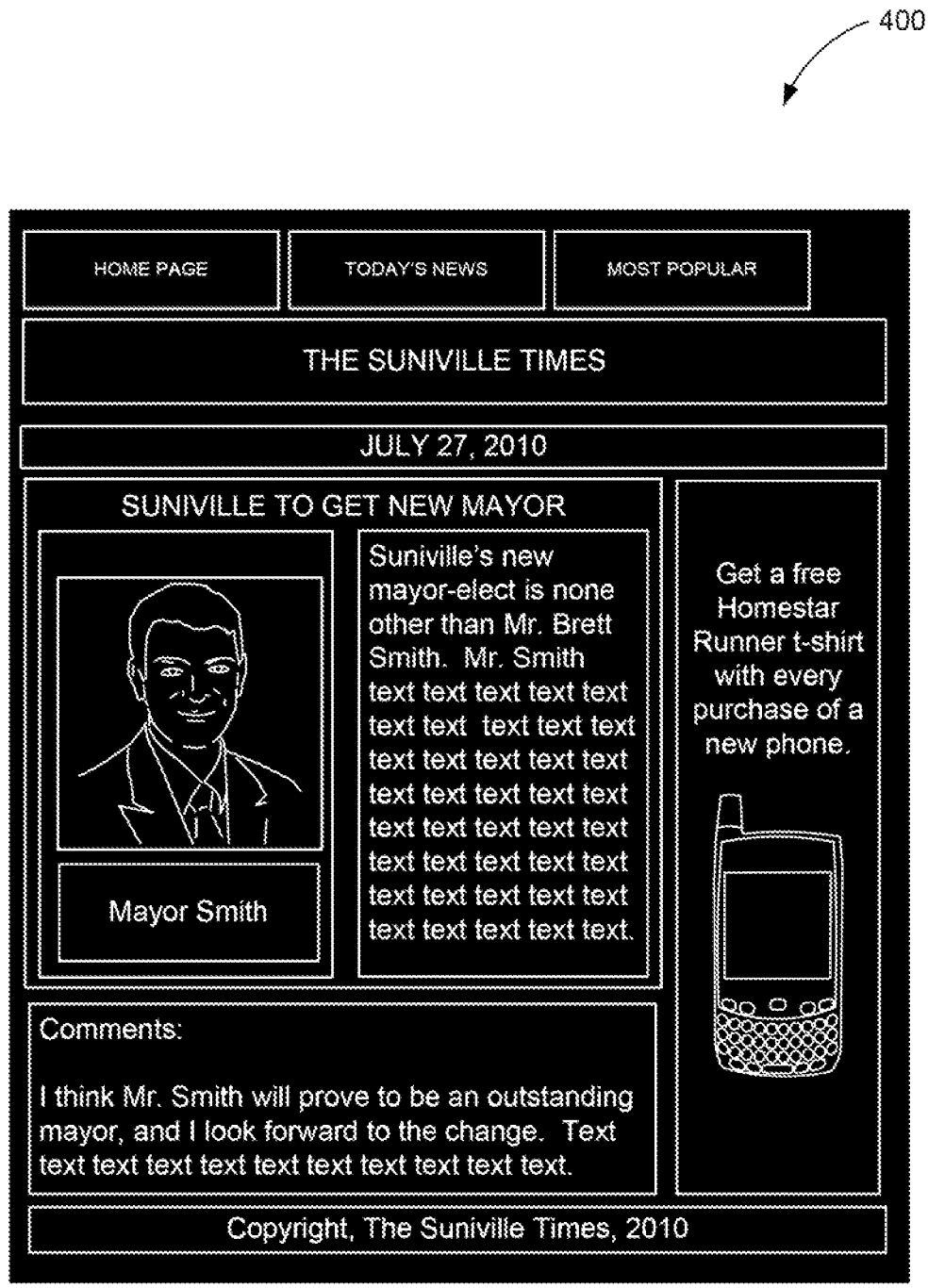
FIG. 4 is a depiction of an edge image based on the grayscale rendered image of FIG. 3, according to one example of principles described herein.

After obtaining an image (e.g., a grayscale image) of the rendered web page, the processor (125) may apply an edge detection operator to the image to detect the edges of regions within the image of the rendered web page (110). FIG. 4 is a depiction of an edge image (400) based on the grayscale rendered image (300) of FIG. 3, according to one example of principles described herein. The edge detection operator may be, for example, a Canny operator, or a Sobel operator, among others. The edge image (400) of FIG. 4 is the corresponding edge image of FIG. 3 produced by the Canny operator. Further, in one example, color edge detectors may be used in instances in which the rendered web page (110) is converted into a color image.

Figure 5:
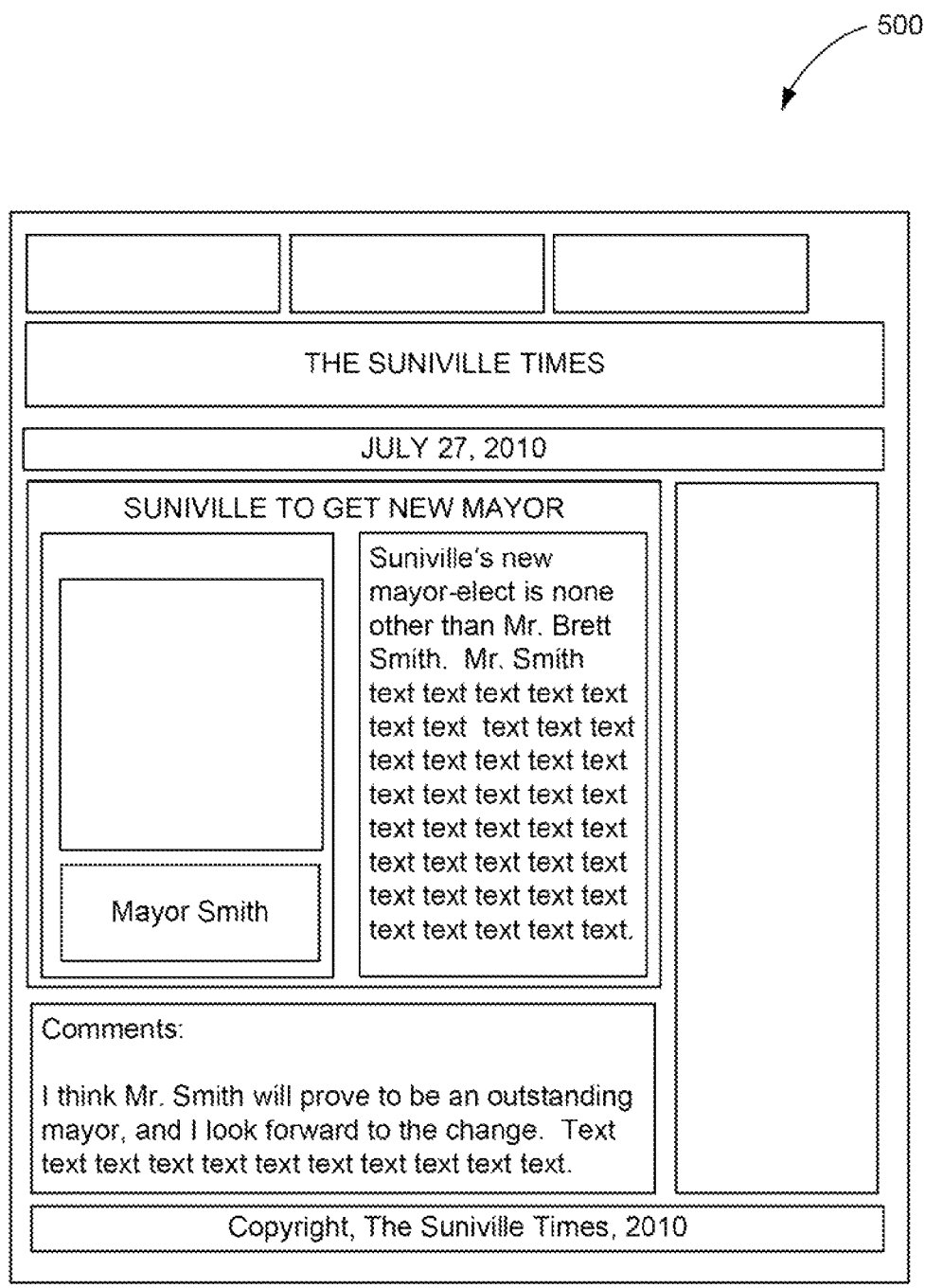
FIG. 5 is a depiction of the edge image of FIG. 4 after filtering and removing edges belonging to non-separator line elements within the edge image, according to one example of principles described herein.

Next, once the edge image is generated, and edges within the edge image are detected (Step 215), several edges belonging to non-separator lines are filtered (Steps 220, 225, and 230). FIG. 5 is a depiction of the edge image (400) of FIG. 4 after filtering and removing edges belonging to non-separator line elements within the edge image (500), according to one example of principles described herein. More specifically, in Step 220, edges belonging to web control elements are filtered. The processor (125) detects and removes all the edge pixels within the bounding box of web control elements. This step is performed because separator lines are not in web control elements within the web page (110).

Next, edges belonging to web image elements are filtered (Step 225). The processor (125) detects and removes all the edge pixels within the bounding box of web image elements. This step is performed because, like web control elements, separator lines are not in web image elements within the web page (110). Next, in a similar fashion, edges belonging to web text elements are filtered (Step 230). The processor (125) detects and removes all the edge pixels within the bounding box of web text elements. Further, the web text elements' bounding boxes may not be accurate and may overflow to larger areas than the text's actual location. Therefore, in one example it is detected whether the bounding box is accurate. The processor (125) only removes edge pixels inside accurate bounding boxes of web text elements. Otherwise, the processor (125) removes, separator lines that overlap with the inaccurate bounding box of web text elements.

Figure 6:
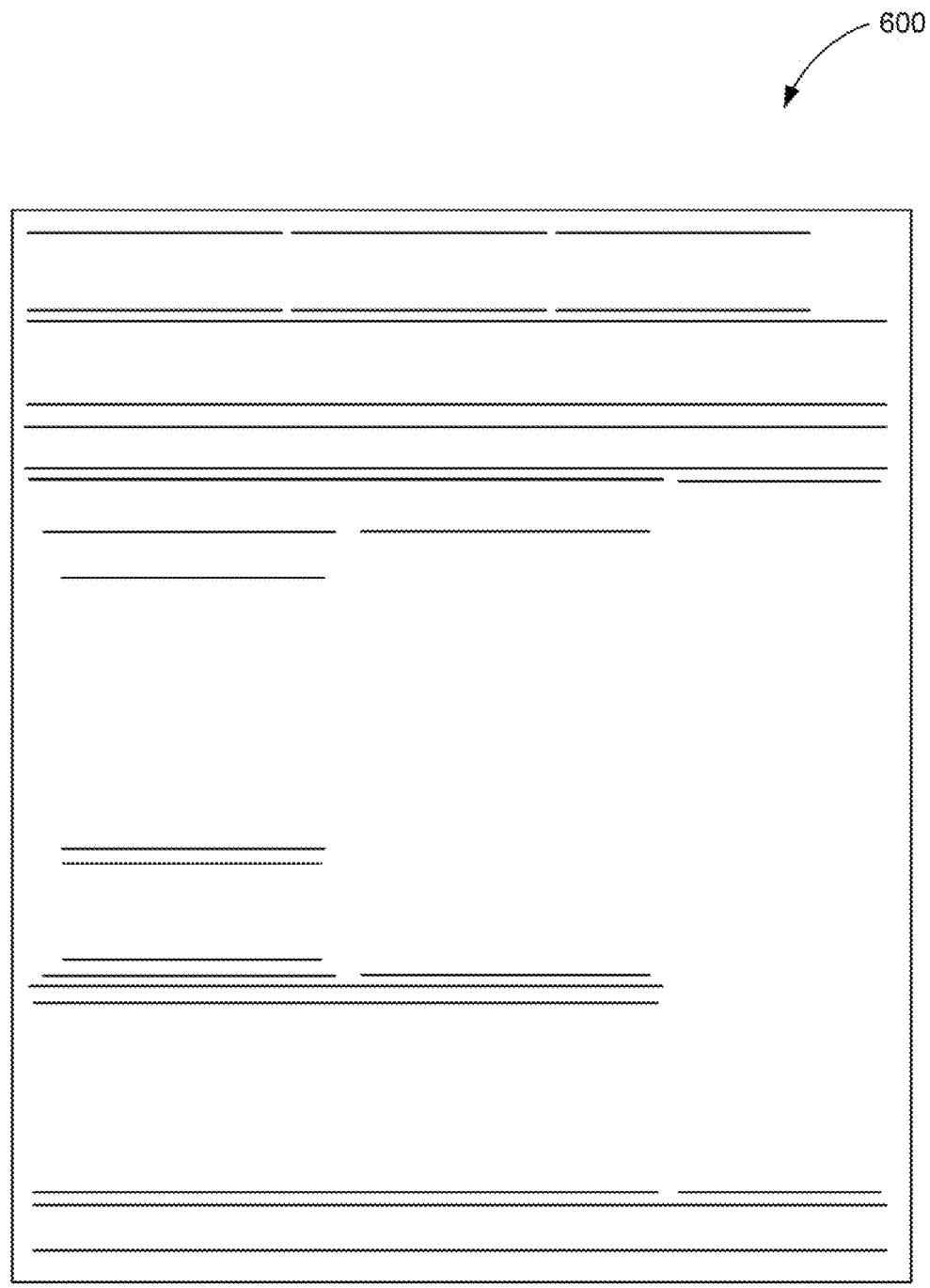
FIG. 6 is a depiction of the edge image of FIGS. 4 and 5 after detecting horizontal lines within the edge image, according to one example of principles described herein.

After filtering of non-separator line elements (Steps, 220, 225, 230), the horizontal lines within the edge image are detected (Step 235). In one example, the horizontal lines are detected by application of an erosion-dilation operator by the processor (125). The erosion operation, and then the dilation operation are performed on the edge image. By application of the erosion-dilation operator, broken horizontal lines can be detected. The results of application of an erosion-dilation operator in detecting the horizontal lines within the edge image (600) are depicted in FIG. 6.

Figure 7:
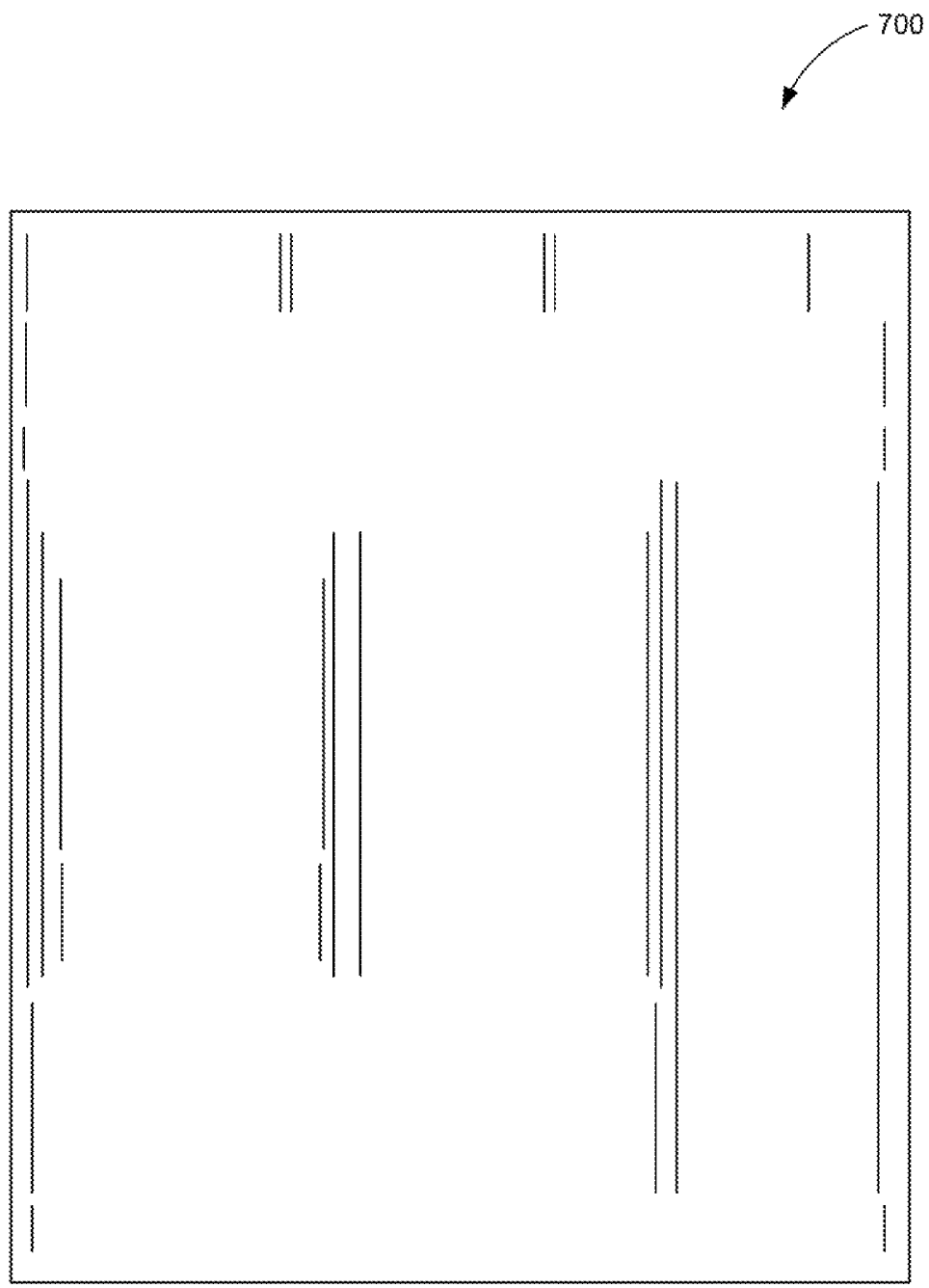
FIG. 7 is a depiction of the edge image of FIGS. 4 and 5 after detecting vertical lines within the edge image, according to one example of principles described herein.

Next, in a similar fashion, the vertical lines within the edge image are detected (Step 240). In one example, the vertical lines are detected by application of an erosion-dilation operator by the processor (125). The erosion operation, and then the dilation operation are performed on the edge image. By application of the erosion-dilation operator, broken vertical lines can be detected. The results of application of an erosion-dilation operator in detecting the vertical lines within the edge image (700) are depicted in FIG. 7. The erosion-dilation operator for vertical line detection can be designed differently with respect to the operator for horizontal line detection.

Figure 8:
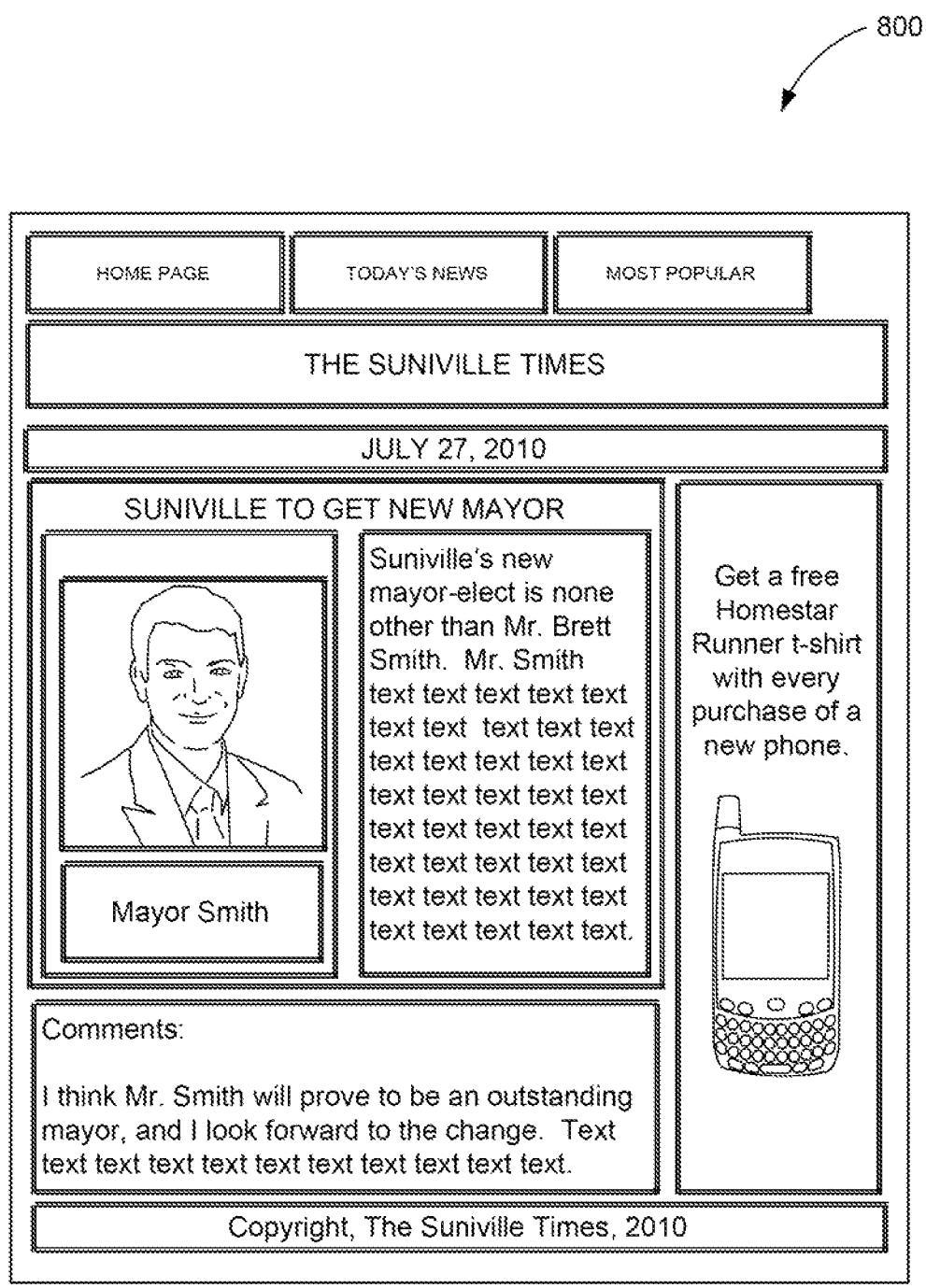
FIG. 8 is a depiction of a resulting image including separator lines based on the edge image of FIGS. 4, 5, 6, and 7 after short lines have been filtered, according to one example of principles described herein.

Finally, after detecting horizontal and vertical within the edge image (Steps 235, 240), short lines within the edge image are filtered (Step 245). A predetermined threshold may be applied to filter out very short lines, which are not, or should not be classified as separator lines. In one example, the threshold can be user-defined in light of the experience of the user. In another example, the threshold can be adaptively computed. As a result of the above method, FIG. 8 depicts the final detection results of separator lines (800).

Systems and methods of detecting separator lines in a web page are described herein. In an example, separator lines are detected by determining coordinates of visible web elements on a web page, generating an edge image of the web page based on the coordinates of the web elements, filtering edges belonging to non-separator line elements within the edge image, detecting horizontal lines within the edge image, detecting vertical lines within the edge image, and filtering short lines within the edge image. This detecting of separator lines in a web page may have a number of advantages, including: (1) being able to detect separator lines in a web page through an image processing approach, (2) producing separator line detection results that are more accurate and meaningful because of the use of web page information such as coordinates of web elements; and (3) filtering of remaining text edges as well as detection of slashed lines are more accurately performed via the erosion and dilation operators utilized. Being able to detect separator lines within the web pages is very useful in subsequent processing of a web page including, for example, web page printing, block level based web page searching, web page segmentation, and many other applications.

The preceding description has been presented only to illustrate and describe examples and examples of the principles described. This description is not intended to be exhaustive or to limit these principles to any precise form disclosed. Many modifications and variations are possible in light of the above teaching.

What is claimed is:

1. A method performed by a physical computing device comprising at least one processor for detecting separator lines in a web page comprising:
   determining, with the computing system, coordinates of visible web elements on a web page;
   generating, with the computing system, an edge image of the web page based on the coordinates of the web elements;
   filtering, with the computing system, edges belonging to non-separator line elements within the edge image;
   detecting, with the computing system, horizontal lines within the edge image;
   detecting, with the computing system, vertical lines within the edge image; and
   filtering, with the computing system, short lines within the edge image to provide an indication of the separator lines.

2. The method of claim 1, in which determining coordinates of visible web elements on a web page comprises:
   querying each of a plurality of text nodes of a data structure representing the web page;
   wrapping each of the plurality of text nodes in a pair of mark-up language tags;
   obtaining the co-ordinates of a bounding rectangle for each text node using the mark-up language tags;
   attaching an attribute specifying the coordinates of the bounding rectangle to each text node; and
   determining whether each text node is invisible, and if it is invisible, excluding it from an output data structure comprising the plurality of text nodes and attached attribute.

3. The method of claim 1, in which generating an edge image of the web page based on the coordinates of the web elements comprises:
   converting the web page into an image; and
   applying an edge detection operator to the image in which the edge detection operator determines the edges of the web page.

4. The method of claim 3, in which the image is at least one of a grayscale image, a color image, and a binary image.

5. The method of claim 1, in which filtering edges belonging to non-separator line elements within the edge image of the web page comprises:
   filtering edges belonging to web control elements within the edge image of the web page;
   filtering edges belonging to web image elements within the edge image of the web page; and
   filtering edges belonging to text elements within the edge image of the web page.

6. The method of claim 5, in which filtering edges belonging to web control elements within the edge image of the web page comprises removing all edge pixels within the bounding box of web control elements.

7. The method of claim 5, in which filtering edges belonging to web image elements within the edge image of the web page comprises removing all edge pixels within the bounding box of web image elements.

8. The method of claim 5, in which filtering edges belonging to text elements within the edge image of the web page comprises removing all edge pixels within non-overflowing bounding boxes of web text elements and keeping the edge pixels within the overflow bounding box of web text elements which may overlap with separator lines.

9. A system for detecting separator lines in a web page comprising:
   a memory device; and
   a processor communicatively coupled to the memory, in which the processor:
   determines coordinates of visible web elements on a web page;
   generates an edge image of the web page based on the coordinates of the web elements;
   filters edges belonging to non-separator line elements within the edge image;
   detects horizontal lines within the edge image;
   detects vertical fines within the edge image; and
   filters short lines within the edge image to provide an indication of the separator lines.

10. The system of claim 9, in which the processor further:
    converts the web page into an image; and
    applies an edge detection operator to the image in which the edge detection operator determines the edges of the web page.

11. The system of claim 10, in which the image is at least one of a grayscale image, a color image, and a binary image.

12. The system of claim 9, in which the processor further:
    filters edges belonging to web control elements within the edge image of the web page;
    filters edges belonging to web image elements within the edge image of the web page; and
    filters edges belonging to text elements within the edge image of the web page.

13. The system of claim 12, in which the image processor filters edges belonging to web control elements within the edge image of the web page by removing all edge pixels within the bounding box of web control elements.

14. The system of claim 12, in which the image processor filters edges belonging to web image elements within the edge image of the web page by removing all edge pixels within the bounding box of web image elements.

15. The system of claim 12, in which the image processor filters edges belonging to text elements within the edge image of the web page by removing all edge pixels within non-overflow bounding boxes of web text elements and keeping the edge pixels within the overflow bounding box of web text elements which may overlap with separator lines.

16. A computer program product for detecting separator lines in a web page, the computer program product comprising:
    a non-transitory computer usable medium having computer usable program code embodied therewith, the computer usable program code adapted to be executed by a computing device to implement a method comprising:

determining coordinates of visible web elements on a web page;

generating an edge image of the web page based on the coordinates of the web elements;

filtering edges belonging to non-separator line elements within the edge image;

detecting horizontal lines within the edge image;

detecting vertical lines within the edge image;

filtering short lines within the edge image to provide an indication of the separator lines.

17. The computer program product of claim 16, in which generating an edge image of the web page based on the coordinates of the web elements comprises:

converting the web page into an image; and applying an edge detection operator to the image in which the edge detection operator determines the edges of the web page.

18. The computer program product of claim 17, in which the image is at least one of a grayscale image, a color image, and a binary image.

19. The computer program product of claim 16, in which filtering edges belonging to non-separator line elements within the edge image comprises:

filtering edges belonging to web control elements within the edge image of the web page;

filtering edges belonging to web image elements within the edge image of the web page; and filtering edges belonging to text elements within the edge image of the web page.

20. The computer program product of claim 16, in which determining coordinates of visible web elements on a web page comprises:

querying each of a plurality of text nodes of a data structure representing the web page;

wrapping each of the plurality of ext nodes in a pair of mark-up language tags;

obtaining the co-ordinates of a bounding rectangle for each text node using the mark-up language tags;

attaching an attribute specifying the coordinates of the bounding rectangle to each text node; and determining whether each text node is invisible, and if it is invisible, excluding it from an output data structure comprising the plurality of text nodes and attached attribute.

\* \* \* \* \*

UNITED STATES PATENT AND TRADEMARK OFFICE
CERTIFICATE OF CORRECTION

| | |
|---|---|
| PATENT NO. | : 8,867,837 B2 |
| APPLICATION NO. | : 13/812421 |
| DATED | : October 21, 2014 |
| INVENTOR(S) | : Hui-Man Hou et al. |

Page 1 of 1

It is certified that error appears in the above-identified patent and that said Letters Patent is hereby corrected as shown below:

In the Claims,

In column 8, line 29, in Claim 9, delete "fines" and insert -- lines --, therefor.

In column 10, line 13, in Claim 20, delete "ext" and insert -- text --, therefor.

Signed and Sealed this
Third Day of March, 2015

Michelle K. Lee
*Deputy Director of the United States Patent and Trademark Office*